United States Patent
Laffitte et al.

(10) Patent No.: US 11,447,450 B2
(45) Date of Patent: Sep. 20, 2022

(54) PROCESS FOR PRODUCING SULFONIC ACID

(71) Applicant: ARKEMA FRANCE, Colombes (FR)

(72) Inventors: Jean-Alex Laffitte, Biarritz (FR); Bernard Monguillon, Nogent sur Marne (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/643,083

(22) PCT Filed: Aug. 30, 2018

(86) PCT No.: PCT/FR2018/052127
§ 371 (c)(1),
(2) Date: Feb. 28, 2020

(87) PCT Pub. No.: WO2019/043339
PCT Pub. Date: Mar. 7, 2019

(65) Prior Publication Data
US 2020/0347014 A1    Nov. 5, 2020

(30) Foreign Application Priority Data
Sep. 1, 2017 (FR) ...................................... 1758099

(51) Int. Cl.
*C07C 303/42* (2006.01)

(52) U.S. Cl.
CPC .................. *C07C 303/42* (2013.01)

(58) Field of Classification Search
CPC ... C07C 303/22; C07C 303/42; C23F 11/163; C23F 11/04; C23F 11/181
See application file for complete search history.

(56) References Cited

U.S. PATENT DOCUMENTS

| | | | |
|---|---|---|---|
| 2,455,659 A | 12/1948 | Duncan et al. | |
| 2,534,201 A * | 12/1950 | Hutter | C23F 11/02 206/524.3 |
| 3,505,367 A | 4/1970 | Brunei | |
| 3,759,594 A * | 9/1973 | Cobb | A45D 27/22 312/31 |
| 5,055,230 A * | 10/1991 | Clubley | C07D 319/12 252/389.62 |
| 6,120,619 A | 9/2000 | Goudiakas et al. | |
| 6,329,073 B1 * | 12/2001 | Deruyck | C10M 129/38 428/621 |
| 2011/0108120 A1 | 5/2011 | Fassbender et al. | |
| 2017/0216550 A1* | 8/2017 | Meyerhoff | A61M 1/342 |
| 2020/0181072 A1 | 6/2020 | Laffitte et al. | |

FOREIGN PATENT DOCUMENTS

| | | | |
|---|---|---|---|
| BE | 613 776 A | 8/1962 | |
| EP | 0 931 854 A1 | 7/1999 | |
| GB | 519823 * | 4/1940 | |
| KR | 100486103 B1 * | 9/2005 | ......... B01D 46/0032 |
| WO | WO-8904856 A1 * | 6/1989 | ............... C09D 5/08 |
| WO | WO-2006086875 A1 * | 8/2006 | ............... C11D 3/28 |

OTHER PUBLICATIONS

International Search Report for PCT/FR2018/052127, dated Nov. 23, 2018 (4 pages with English translation).
Written Opinion for PCT/FR2018/052127, dated Nov. 23, 2018 (5 pages).
Gaur, B., et al. Corrosion of metals and alloys in methane sulphonic acid. British Corrosion Journal. 1999. vol. 34, No. 1, pp. 63-66.

* cited by examiner

*Primary Examiner* — Rosalynd A Keys
(74) *Attorney, Agent, or Firm* — Smith, Gambrell & Russell, LLP; Dennis C. Rodgers; Ram W. Sabnis

(57) ABSTRACT

The subject of the present invention is a process for producing a sulfonic acid which is sparingly corrosive, or even non-corrosive, with respect to stainless steels, said process comprising at least the steps of adding at least one nitrite to a sulfonic acid, curing, with stirring, with sparging of the mixture and recovering the low-corrosion sulfonic acid obtained.
The invention also relates to the low-corrosion sulfonic acid obtained according to the process of the invention, and also to the use thereof as low-corrosion sulfonic acid.

24 Claims, No Drawings

PROCESS FOR PRODUCING SULFONIC ACID

The present invention relates to the field of the protection of metals from corrosion against acid attacks, and in particular a process for producing a sulfonic acid which is sparingly corrosive, or even non-corrosive, with respect to metals and in particular stainless steels.

Sulfonic acids, and in particular sulfonic acids termed organic, such as for example methanesulfonic acid (MSA), para-toluenesulfonic acid (PTSA), benzenesulfonic acid (BS) or trifluoromethane sulfonic acid, are strong acids widely used in numerous applications, in particular in catalysis and in surface treatment, such as galvanoplasty, stripping, cleaning or descaling, to cite just the main examples, without being limited thereto.

However, it has been observed that aqueous solutions of such sulfonic acids corrode metals, the corrosion rates depending simultaneously on the acid concentration, on the temperature and on the nature of the metal. For example, at ambient temperature, stainless steel of 304L or 1.4307 type is corrodible at MSA concentrations greater than 5% by weight in water. Such corrosion risks are unacceptable in many applications, and particularly for the storage of these acids mainly when they are in aqueous solution.

In order to make sulfonic acids barely corrosive, or even non-corrosive, towards metals, and particularly towards stainless steels, numerous studies have already been carried out, among which one technique, which has shown satisfactory results, consists of the addition of nitrates to said acids. This method is in particular described by B. Gaur and H. S. Srinivasan ("*British Corrosion Journal*", 34(1), (1999), 63-66) who showed that the addition of ferric ions or nitrates makes it possible to produce an inhibitory effect on corrosion by MSA on various steels.

Other solutions have been studied, among which mention may for example be made of that described in application EP 0 931 854, which proposes inhibiting the corrosion of stainless steels in organosulfonic acid medium, by adding at least one oxidizing agent chosen from salts or oxides of cerium(IV), of iron(III), of molybdenum(VI), of vanadium (V), nitrites and persulfates. However, the addition of some of these inhibitors, such as nitrites, generally results in nitrogen oxides (NOx) being given off, said nitrogen oxides possibly proving to be dangerous or at the very least harmful and toxic both to operators and to users, and also to the environment. This patent application is in particular silent with regard to how to produce nitrite/sulfonic acid mixtures without causing NOx to be given off.

Thus, there consequently remains a need for a process for producing a sulfonic acid which is sparingly corrosive, or even non-corrosive (termed "low-corrosion" sulfonic acid) with respect to metals, and in particular stainless steels, said process being less toxic and less harmful to operators, to users and to the environment, compared with the processes known from the prior art.

The applicant has now discovered, surprisingly, that the addition of a corrosion inhibitor under specific and suitable conditions makes it possible to overcome the drawbacks described above. The applicant has therefore carried out a process for producing a sulfonic acid which satisfies these specific conditions and the implementation of which will emerge in the light of the description that follows.

Thus, a first subject of the invention relates to a process for producing a low-corrosion sulfonic acid, comprising at least the following steps:

a) adding at least one nitrite to a conventional sulfonic acid;
b) curing the mixture obtained in step a) at a temperature between 0° C. and 100° C., and preferably between 0° C. and 80° C., more particularly between 10° C. and 60° C., even more particularly between 10° C. and 50° C., for a period of between a few seconds and a few hours, preferably between 1 min and 4 h, more particularly between 10 min and 2 h, even more particularly between 10 min and 1 h;
c) recovering the low-corrosion sulfonic acid.

In the present invention, the term "low-corrosion sulfonic acid" is intended to mean a sulfonic acid of which the potential remains virtually at the same level and does not rise back up after applying an amount of current of −800 $\mu A \cdot cm^{-2}$, for 1 minute, then stopping the application of this current, as explained below in the "low-corrosion" validation test protocol. In other words, a low-corrosion sulfonic acid according to the present invention remains in the passive state after application of a current of −800 $\mu A \cdot cm^{-2}$, for 1 minute, whereas a sulfonic acid not in accordance with the present invention (corrosive) returns to the active state (corrosion) after depassivation by application of said amount of current of −800 $\mu A \cdot cm^{-2}$, for 1 minute.

In the present invention, the nitrite, used as corrosion inhibitor, may be any nitrite known to those skilled in the art, and is preferably chosen from alkali metal or alkaline-earth metal nitrites, or else ammonium nitrite. Among the alkali metal nitrites, sodium nitrite and potassium nitrite are preferred. According to one preferred embodiment of the invention, sodium nitrite is used. Other nitrites can be used; however, for obvious reasons of costs, availability and environmental protection, the use of metal nitrites such as, for example, copper nitrite or other heavy metal nitrites will be avoided.

In the present invention, by "conventional sulfonic acid" it may be understood every sulfonic acid known to those skilled in the art which does not comprise a corrosion inhibitor, in particular a corrosion inhibitor as defined above. For example, it can be a sulfonic acid which has not been chemically or physically processed in order to confer to it anticorrosive properties with respect to metals, and stainless steels as mentioned above. In particular, by "conventional sulfonic acids" it may be understood sulfonic acids of formula R—$SO_3H$, where R represents a linear, branched or cyclic, saturated or unsaturated hydrocarbon-based chain comprising from 1 to 12 carbon atoms, which is unsubstituted or substituted with one or more radicals and/or atoms chosen from halogen (such as fluorine, chlorine or bromine) atoms, alkyl radicals containing from 1 to 6 carbon atoms and aryl and heteroaryl radicals comprising 6 or 10 ring members which do not comprise a corrosion inhibitor, in particular a corrosion inhibitor as defined above. In one embodiment, the "conventional sulfonic acids" are not low-corrosion sulfonic acids such as defined above.

In the present invention, the term "sulfonic acid" is intended to mean any sulfonic acid known to those skilled in the art and more particularly the sulfonic acids of formula R—$SO_3H$, where R represents a linear, branched or cyclic, saturated or unsaturated hydrocarbon-based chain comprising from 1 to 12 carbon atoms, which is unsubstituted or substituted with one or more radicals and/or atoms chosen from halogen (such as fluorine, chlorine or bromine) atoms, alkyl radicals containing from 1 to 6 carbon atoms and aryl and heteroaryl radicals comprising 6 or 10 ring members.

The term "alkyl" is intended to mean a linear or branched, saturated hydrocarbon-based radical. The term "aryl" is intended to mean an aromatic radical, preferably a phenyl or naphthyl radical, more preferentially a phenyl radical. The term "heteroaryl" is intended to mean an aromatic radical having one or more heteroatoms chosen from oxygen, nitrogen and sulfur.

Preferably, R represents a hydrocarbon-based chain comprising from 1 to 6 carbon atoms, more particularly chosen from methyl, ethyl, n-propyl, iso-propyl, n-butyl, iso-butyl, sec-butyl, tert-butyl, linear or branched pentyl radicals, linear or branched hexyl radicals, and phenyl and naphthyl radicals.

Thus, and in a non-limiting manner, the sulfonic acids included in the context of the present invention are preferably chosen from methanesulfonic acid, ethanesulfonic acid, n-propanesulfonic acid, iso-propanesulfonic acid, n-butanesulfonic acid, iso-butanesulfonic acid, sec-butanesulfonic acid, tert-butanesulfonic acid, trifluoromethanesulfonic acid, para-toluenesulfonic acid, benzenesulfonic acid, naphthalenesulfonic acid, and mixtures of two or more of them in any proportions.

According to one most particularly preferred embodiment, the sulfonic acid used in the context of the present invention is methanesulfonic acid, ethanesulfonic acid, trifluoromethanesulfonic acid or para-toluenesulfonic acid; entirely preferably, the sulfonic acid is methanesulfonic acid.

The sulfonic acid used in the context of the present invention may be sulfonic acid alone or a mixture of two or more sulfonic acids, optionally in a solvented medium and optionally as a mixture with one or more additives and/or fillers well known to those skilled in the art.

Thus, the sulfonic acid(s) may be in solvented medium, said solvent possibly being water or an organic solvent or a mixture of organic solvents, or else water as a mixture with one or more other organic solvents. As a general rule, the concentration of sulfonic acid(s) in the solvent(s) is between 0.01% and 100%, limits inclusive, by weight of sulfonic acid(s) relative to the total weight of sulfonic acid(s) in solvented medium, it being understood that, when the concentration is equal to 100%, the amount of solvent is zero or negligible or undetectable. Preferably, this concentration is between 0.01% and 99.99%, preferably between 0.1% and 99.9%, more preferably between 0.5% and 75%, limits inclusive, by weight of sulfonic acid(s) relative to the total weight of sulfonic acid(s) in solvented medium.

The organic solvents indicated above and that can be used to solvent the sulfonic acid(s) may be of any type known to those skilled in the art, and preferably water-soluble organic solvents, such as alcohols, sulfoxides, mineral or organic acids, more preferentially methanol, ethanol, dimethyl sulfoxide, sulfuric acid, to cite just the most common ones and the most well-known ones among them.

The additives and fillers that may be present as a mixture with the sulfonic acids may for example be, in a non-limiting manner, one or more additives and/or fillers chosen from viscosity or rheology modifiers, foaming agents, anti-foams, surfactants, disinfectants, biocides, stabilizers, oxidizing agents, enzymes, pigments, dyes, fire retardants, flame retardants, fragrances, aromas, and the like.

These various additives and fillers are present in amounts well known to those skilled in the art, which can vary as a function of the effect desired, of the nature of the sulfonic acid used and of the application considered for said sulfonic acid used.

Step a) of the process according to the invention comprises adding at least one nitrite (or a solution comprising at least one nitrite) to a sulfonic acid (or a solution comprising at least one sulfonic acid). It is particularly preferred to add said at least one nitrite to sulfonic acid and not the reverse. This is because the addition may be more or less exothermic, and the addition of sulfonic acid to the nitrite may result in a very rapid and significant increase in the temperature and may consequently potentially cause a decomposition of the nitrite, and/or in a vaporization of said nitrite.

Said at least one nitrite is added to the sulfonic acid in such a way that the nitrite/sulfonic acid molar ratio is between 200 ppm and 6000 ppm, preferably between 400 ppm and 2000 ppm, in particular between 500 ppm and 1900 ppm.

The nitrite may be added in pure form or in solution in water, or any organic or mineral solvent medium, and in particular an alcohol or sulfuric acid. When the nitrite is a solution in an alcohol, the alcohol used may be any type of alcohol comprising from 1 to 6 carbon atoms, preferably methanol or ethanol.

The addition according to step a) of the process according to the present invention is generally carried out with more or less vigourous stirring, depending on the viscosity of the reaction medium, and depending on the rate of addition and of homogenization desired. It is in fact important to carry out the addition and the homogenization sufficiently slowly to avoid any problems of decomposition and/or vaporization of the nitrite, as indicated above.

Without being bound by theory, it has been discovered that the required "curing" step b) (also called "baking" step) allows perfect homogenization of the nitrite in the sulfonic acid and "activation" of said nitrite making it possible to confer on the sulfonic acid its "low-corrosion" property as indicated above.

According to one embodiment, the "curing" step b) is performed during from 1 h to 5 h, preferably from 1 h to 4 h, for example 3 h.

Step b) is advantageously carried out with stirring according to any means known to those skilled in the art, when it is a question of stirring a mixture comprising a strong acid heated to the curing temperature set out above.

The curing performed in step b) can result in the formation of nitrogen oxides (subsequently denoted "NOx"), which can escape from the reaction medium and can possibly be visually observed in the form of reddish brown vapours being given off from the reaction medium. For obvious security and safety reasons, these NOx can advantageously be suctioned off and discharged for treatment, for example by scrubbing out, preferably scrubbing out with an aqueous base such as a sodium hydroxide solution, which will be treated before being discharged into the environment, according to the conventional techniques known to those skilled in the art.

According to one advantageous embodiment of the process according to the present invention, the mixture obtained after the curing of step b), or else during the curing of step b), or else during and after the curing of step b), is subjected to a step which makes it possible to facilitate and/or accelerate the removal of all or part of the NOx formed during the curing of step b).

The removal of all or part of the NOx formed can be carried out according to any means known to those skilled in the art, and for example by stripping, bubbling or sparging. The latter methods consist in bubbling air and/or an inert gas, preferably a gas which is inert in the reaction mixture during and/or after step b). According to one most particularly preferred embodiment of the process of the present invention, the inert gas used is nitrogen. The amount and the flow rate of air and/or of inert gas used depend on many factors, such as the amount of reaction medium, the nitrite concentration and the sulfonic acid concentration. Those skilled in the art will know how to easily adjust said amount and the flow rate of air and/or of inert gas to be used.

By way of example, when the removal of the NOx is performed by bubbling with air or an inert gas, preferably an inert gas, the bubbling is carried out on the mixture resulting from step b), for example at a temperature between 0° C. and 100° C., preferably between 0° C. and 80° C., more particularly between 10° C. and 60° C., even more particularly between 10° C. and 50° C., for a period of between a few minutes and a few hours, preferably between 10 min and 12 hours, more particularly between 15 min and 8 hours, even more particularly between 30 min and 7 hours, for example between 30 minutes and approximately 6 hours.

The step of removing the NOx can be performed one or more times, in a manner which is continuous, sequenced or alternating or even concomitant with step b) of curing the mixture. It is preferred to carry out the step of removing all or part of the NOx in one go during the curing step b). According to another preferred embodiment, the step of removing all or part of the NOx is carried out in one go after the curing step b).

The process according to the invention can be carried out batchwise or continuously. In the case of a continuous process, the sulfonic acid and the nitrite are preferably added in countercurrent mode. In the case of a batchwise process, the reactor can be equipped with any type of stirring, such as an anchor or impeller, and stirring by external loop.

The process according to the invention thus makes it possible to obtain a low-corrosion sulfonic acid, said sulfonic acid comprising only a small amount of nitrites, which does not in any way impair said sulfonic acid, which can thus be used like any conventional sulfonic acid, said acid having the advantage of not corroding, and of corroding very weakly, metals and in particular metals and alloys which can be passivated, in particular based on iron, nickel, titanium, copper, aluminium, molybdenum, manganese, lead, and alloys thereof, and also pairs of these metals or alloys obtained by contact (crimping, riveting, bolting, welding, brazing), especially stainless steels, and in particular the common stainless steels (for example of AISI 304L and AISI 316L type), but also more generally any stainless steel as defined in the standard NF EN 10088-1.

A second subject of the present invention relates to a low-corrosion sulfonic acid substantially obtained according to the process described above. Said acid according to the invention shows entirely notable properties in that it is sparingly corrosive, or even non-corrosive, with respect to metals and in particular stainless steels such as, for example, ferritic, martensitic, austenitic and duplex stainless steels. Among the austenitic stainless steels, AISI 304L steel and AISI 316L steel will be more particularly retained.

A third subject of the present invention relates to the use of said low-corrosion sulfonic acid produced according to the process described above, for limiting, or even preventing, the corrosion of metals by sulfonic acids.

The invention will be understood more clearly by means of the examples which follow, said examples not being in any way limiting, and serving solely to illustrate the invention.

EXAMPLES

The sulfonic acid used in the following examples is 70% methanesulfonic acid (MSA), that is to say methanesulfonic acid diluted to 70% by weight in water.

Example 1

Process without Sparging 135 g of MSA are introduced at 20° C. into a 250 ml round-bottomed three-necked flask connected to a water-cooled reflux condenser (itself connected to a container flask followed by a trap containing sodium hydroxide (NaOH), then a trap containing potassium permanganate ($KMnO_4$)), a tube for introducing nitrogen and a neck for adding sodium nitrite ($NaNO_2$), and said MSA is stirred (400 revolutions per minute or rpm).

0.24 ml (i.e, 0.30375 g) of a solution of $NaNO_2$ at 40% by weight in water is then added, over the course of 1 minute and by means of an automatic pipette. The $NaNO_2$/MSA molar ratio is 1800 ppm. The $NaNO_2$ could also be added in solid form (0.1215 g).

The round-bottomed flask is immediately closed with a stopper and stirring is carried out (400 rpm) for 60 min at 20° C. The low-corrosion MSA obtained is then recovered.

Example 2

Process According to the Invention (With Sparging)

135 g of MSA are introduced at 20° C. into a 250 ml round-bottomed three-necked flask connected to a water-cooled reflux condenser (itself connected to a container flask followed by a trap containing NaOH, then a trap containing $KMnO_4$), a tube for introducing nitrogen and a neck for adding $NaNO_2$, and said MSA is stirred (400 rpm).

0.24 ml (i.e, 0.30375 g) of a solution of $NaNO_2$ at 40% by weight in water is then added, over the course of 1 minute and by means of an automatic pipette. The $NaNO_2$/MSA molar ratio is 1800 ppm.

The round-bottomed flask is immediately closed with a stopper and stirring is carried out (400 rpm) for 60 min at 20° C.

One part of the mixture is subjected to a sparging step for 240 min at 20° C. and the second part of the mixture is subjected to a sparging step for 360 min at 20° C. The sparging is bubbling of nitrogen into the reaction medium with a nitrogen flow rate of approximately 30 ml/minute. The low-corrosion MSAs obtained are then recovered.

Example 3

NOx Measurement

Quantitative determination of the NOx is carried out on each of the three low-corrosion MSAs previously obtained.

100 g of low-corrosion MSA to be quantitatively determined are weighed into a 500 ml two-necked round-bottomed flask and a magnetic bar is added. The round-bottomed flask is closed with a glass stopper. A tube for analysing the NOx, from the company Draeger, is connected to the overhead of the round-bottomed flask which is heated at 60° C. for 30 minutes.

The overhead is then suctioned with a number of pump strokes determined by the operating mode supplied with the tubes from the company Draeger, and the measurements are read.

The results are presented in table 1 below:

TABLE 1

| Sparging time (in min) | NOx (in ppm by volume) |
|---|---|
| 0 | 35 |
| 240 | 6 |
| 360 | 2 |

It is noted that, without the sparging step, the amount of NOx in the low-corrosion MSA is much higher than in the low-corrosion MSA formulations subjected to sparging. Furthermore, it is noted that, after sparging for 360 min, the amount of NOx present in the low-corrosion MSA formulation is 3 times lower than that present in the low-corrosion MSA formulation previously subjected to sparging for 240 min. This demonstrates the impact of the sparging step on the NOx removal from the MSA and also the impact of the sparging time on NOx production.

Low-Corrosion Sulfonic Acid Validation Test Protocol

In order to verify the "low-corrosion" quality, within the meaning of the present invention, of a sulfonic acid, an electrochemical test is carried out using an assembly of 3 electrodes connected to a Biologic VMP3 potentiostat:
1) reference electrode: saturated calomel electrode or "SCE",
2) working electrode: test specimen of 304L stainless steel, 1 cm$^2$ in size, and
3) platinum counter electrode.

The test specimen of the material to be tested is polished with P400 abrasive paper then passivated for 1 hour in a 10% nitric acid solution at ambient temperature. This allows an identical starting state for all the tests. The temperature of the test is thermostatted at 20° C.±2° C.

The protocol applied comprises the following three steps:
a) monitoring of the rest potential of the working electrode (304L) in the sulfonic acid additivated according to the process of the present invention, that is to say measurement of the potential of the material in the solution as a function of time, for 30 minutes,
b) immersion of the three-electrode system in a standard (i.e. non-additivated) sulfonic acid solution, then application to the working electrode of a current of 800 µA·cm2, for 1 minute in order to depassivate the material artificially by fixing the potential thereof in the corrosion range,
c) immersion of the three-electrode system again in the sulfonic acid solution additivated according to the process of the present invention, and monitoring again of the rest potential of the working electrode, until stabilization thereof.

Results of the Validation Test

In the case of a standard, that is to say non-additivated, methanesulfonic acid in solution at 70% by weight in water, after application of an amount of current of −800 µA·cm$^{-2}$, the potential of the working electrode (test specimen of 304L stainless steel) drops to around −350 mV, which corresponds to the passing of the 304L stainless steel into the active state. When the application of the current is stopped, the potential of the material remains virtually at the same level and does not rise back up. The 304L stainless steel remains in the active state and corrodes.

The behaviour is completely different in a solution at 70% by weight in water of a methanesulfonic acid additivated according to the process of the present invention (Examples 1 and 2 above).

A rest potential of the 304L stainless steel of about 750 mV after 30 minutes is first of all noted. During the application of the current of −800 µA·cm$^{-2}$, the potential of the material drops to around −200 mV (passing of the 304L stainless steel into the active state). When the application of the current is stopped, the potential of the material rises back up very rapidly. It is 780 mV after 2 hours of monitoring the potential and a total absence of corrosion is noted.

In all cases (Examples 1 and 2 above), the sodium nitrite-additivated methanesulfonic acid is a low-corrosion methanesulfonic acid within the meaning of the present invention.

The invention claimed is:

1. Process for producing a low-corrosion sulfonic acid, comprising at least the following steps:
   a) adding at least one nitrite to a conventional sulfonic acid;
   b) curing the mixture with stirring at a temperature between 0° C. and 100° C., for a period of between 1 min and 5 h;
   c) sparging the mixture with air and/or inert gas; and
   d) recovering, in an initial recovery step, the low-corrosion sulfonic acid.

2. Process according to claim 1, in which the nitrite is selected from alkali metal nitrites, alkaline-earth metal nitrites or ammonium nitrite.

3. Process according to claim 1, in which the sulfonic acid is a sulfonic acid of formula R—SO$_3$H, where R is selected from linear, branched or cyclic hydrocarbons having from 1 to 12 carbon atoms.

4. Process according to claim 1, in which the sulfonic acid is selected from methanesulfonic acid, ethanesulfonic acid, n-propanesulfonic acid, iso-propanesulfonic acid, n-butanesulfonic acid, iso-butanesulfonic acid, sec-butanesulfonic acid, tert-butanesulfonic acid, trifluoromethanesulfonic acid, para-toluenesulfonic acid, benzenesulfonic acid, naphthalenesulfonic acid, or mixtures thereof.

5. Process according to claim 1, in which the nitrite/sulfonic acid molar ratio is between 200 ppm and 6000 ppm.

6. Process for producing a low-corrosion sulfonic acid, comprising at least the following steps:
   a) adding at least one nitrite to a conventional sulfonic acid;
   b) curing the mixture with stirring at a temperature between 0° C. and 100° C., for a period of between 1 min and 5 h;
   c) recovering the low-corrosion sulfonic acid, and
   wherein the mixture obtained after the curing of step b), or else during the curing of step b), or else during and after the curing of step b), is subjected to a step of bubbling air and/or inert gas.

7. Process according to claim 1, in which the sulfonic acid is a sulfonic acid of formula R—SO$_3$H, where R is selected from linear, branched or cyclic hydrocarbons having from 1 to 12 carbon atoms, wherein the hydrocarbons are unsubstituted or substituted with one or more radicals and/or atoms selected from halogen atoms, alkyl radicals containing from 1 to 6 carbon atoms, aryl, or heteroaryl radicals having 6 or 10 ring members.

8. Process according to claim 6, wherein the step of bubbling air and/or inert gas is during curing.

9. Process according to claim 1, in which stirring occurs both during steps a) and b).

10. Process according to claim 1, in which mixing occurs during step b) and after completion of step a).

11. Process according to claim 1, in which step b) is initiated only after completion of step a) and the time period for step a) is less than the time period for step b).

12. Process according to claim 1, in which curing is carried out at a temperature between 0° C. and 80° C. for between 1 min and 4 h.

13. Process according to claim 1, in which step a) is carried out in a continuous process wherein the sulfonic acid and the nitrite are added in countercurrent mode.

14. Process according to claim 1, in which curing is carried out at a temperature between 10° C. and 50° C.

15. Process according to claim 1, in which NOx generated during step b) is removed during or after step b) to a level at 6 ppm or below.

16. Process according to claim 2, in which the nitrite is sodium nitrite or potassium nitrite.

17. Process according to claim 1, in which the nitrite/sulfonic acid molar ratio is between 500 ppm and 1900 ppm.

18. Process according to claim 1, in which the sulfonic acid is selected from methanesulfonic acid, ethanesulfonic acid, trifluoromethanesulfonic acid, para-toluenesulfonic acid or mixtures thereof.

19. Process according to claim 1, in which the sulfonic acid is methanesulfonic acid.

20. Process according to claim 1, in which the nitrite/sulfonic acid molar ratio is between 400 ppm and 2000 ppm.

21. Process according to claim 1, wherein the mixture obtained after the curing of step b), or else during the curing of step b), or else during and after the curing of step b), is subjected to a step of bubbling air and/or inert gas.

22. Process according to claim 1, wherein the sparging is carried out for 240 min at 20° C.

23. Process according to claim 1, wherein the sparging is carried out for 360 min at 20° C.

24. Process according to claim 1, wherein the inert gas is nitrogen.

* * * * *